(12) United States Patent
Tanaka et al.

(10) Patent No.: US 9,645,100 B2
(45) Date of Patent: May 9, 2017

(54) X-RAY FLUORESCENCE ANALYSIS APPARATUS

(71) Applicant: HITACHI HIGH-TECH SCIENCE CORPORATION, Minato-ku, Tokyo (JP)

(72) Inventors: Keiichi Tanaka, Tokyo (JP); Akikazu Odawara, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 151 days.

(21) Appl. No.: 14/579,630

(22) Filed: Dec. 22, 2014

(65) Prior Publication Data

US 2015/0177167 A1    Jun. 25, 2015

(30) Foreign Application Priority Data

Dec. 24, 2013    (JP) .................................. 2013-265681

(51) Int. Cl.
*G01N 23/223*    (2006.01)
*G01N 23/20*    (2006.01)

(52) U.S. Cl.
CPC ..... *G01N 23/20091* (2013.01); *G01N 23/223* (2013.01)

(58) Field of Classification Search
CPC ......... H01L 2924/0002; H01L 2924/00; H01L 23/552; A61B 18/1492; A61B 1/00165;

(Continued)

(56) References Cited

U.S. PATENT DOCUMENTS 2,783,385 A * 2/1957 Wytzes .............. G01N 23/2076
378/145
3,154,684 A * 10/1964 Ziegler ................ G01N 23/203
378/3

(Continued)

FOREIGN PATENT DOCUMENTS

| JP | 0740080 | 12/1987 |
| JP | 0711600 | 1/1990 |
| JP | 2008039500 | 2/2008 |

OTHER PUBLICATIONS

Keiichi Tanaka et al. (nine), "Transition Edge Sensor-Energy Dispersive Spectrometer (TES-EDS) and Its Applications", "IEICE Transactions on Electronics", vol. E92-C No. 3, 2009, p. 334 to 340.

(Continued)

*Primary Examiner* — Irakli Kiknadze
(74) *Attorney, Agent, or Firm* — Adams & Wilks

(57) ABSTRACT

An X-ray fluorescence analysis apparatus is provided with: an excitation source configured to excite an analysis target sample to emit a characteristic X-ray; an X-ray detector configured to detect the characteristic X-ray emitted from the analysis target sample; and an electromagnetic wave shield and a heat shield that are sequentially arranged from the analysis target sample toward the X-ray detector. The electromagnetic wave shield is provided with a through hole portion on which a through hole through which the characteristic X-ray passes is formed, the through hole having a size equal to or smaller than 50 μm. The heat shield is provided with a window portion through which the characteristic X-ray is passed through.

12 Claims, 6 Drawing Sheets

(58) Field of Classification Search
CPC .......... A61B 1/07; A61B 2017/00057; A61B 2017/00061; A61B 2017/00084; A61B 2018/00642; A61B 2018/00761; A61B 2018/00791; A61B 2018/00904; A61B 2090/306; A61B 6/485; A61B 6/4021; G01N 23/20091; G01N 2223/076; G01N 23/223; G01N 2223/506; G01N 23/20; G01N 21/276; G01N 21/278; G01N 21/645; G01N 2201/0221; G01N 2223/307; G01N 2223/31; G01N 23/08; G01N 23/12; G01N 23/20025; G01N 35/00732; G01T 1/24; G01T 1/1606; G01T 1/2928; G01T 1/241; G01T 1/249; G01T 1/006; G01T 1/16; G01T 1/161; G01T 1/1648; G01T 1/17; G01T 1/20; G01T 1/2018; G01T 1/202; G01T 1/247; G01T 1/26; G01T 1/36; G01T 7/00; G01T 1/10; H01J 2235/087; H01J 2235/186; H01J 2237/002; H01J 2237/006; H01J 2237/061; H01J 2237/0807; H01J 2237/2803; H01J 27/022; H01J 27/26; H01J 35/14; H01J 35/32; H01J 37/023; H01J 37/067; H01J 37/08; H01J 37/26; H01J 37/28
USPC .......................... 378/44, 45–50, 70
See application file for complete search history.

(56) References Cited

U.S. PATENT DOCUMENTS

| | | | | |
|---|---|---|---|---|
| 3,262,002 | A | * | 7/1966 | Kreplin .......... H01J 47/02 313/52 |
| 5,880,467 | A | | 3/1999 | Martinis et al. .......... 250/310 |
| 6,230,499 | B1 | * | 5/2001 | Hohne .......... F25B 9/145 374/E17.003 |
| 7,289,597 | B2 | * | 10/2007 | Sasayama .......... G01N 23/2252 378/43 |
| 7,910,888 | B2 | * | 3/2011 | Tanaka .......... G01T 1/1606 250/336.2 |
| 2004/0011960 | A1 | * | 1/2004 | Morooka .......... G01J 1/42 250/336.1 |
| 2005/0184238 | A1 | * | 8/2005 | Odawara .......... G01T 1/1606 250/336.2 |
| 2006/0104419 | A1 | * | 5/2006 | Sasayama .......... G01N 23/207 378/145 |

OTHER PUBLICATIONS

AP Ultra-thin Polymer X-ray Windows. [online]. MOXTEK Incorporated, 2010. "retrieved on Oct. 15, 2013". Retrieved from the Internet: <URL:http://moxtek.com/xray-product/ap-windows/>.
Hiroyasu Hagiwara, "Outline of Cryogenic Engineering", Publishing Office in Tokyo Denki University, 1999, refer to p. 264).

* cited by examiner

Embodiment

Comparison Example

X-RAY FLUORESCENCE ANALYSIS APPARATUS

CROSS-REFERENCE TO RELATED APPLICATION

This application claims priority from Japanese Patent Application No. 2013-265681, filed on Dec. 24, 2013, the entire subject matter of which is incorporated herein by reference.

BACKGROUND

1. Technical Field

The present invention relates an X-ray fluorescence analysis apparatus that is provided with a radiation detector configured by a superconducting transition edge sensor.

2. Description of the Related Art

As an X-ray fluorescence analysis apparatus that is capable of discriminating energy of an X-ray, there are an energy dispersion-type X-ray detector (energy dispersive spectroscopy, hereinafter referred to as EDS) and a wavelength dispersive spectroscopy, hereinafter, referred to as WDS.

The aforementioned EDS is an X-ray detector of a type in which energy of an X-ray taken in a detector is converted into an electrical signal in the detector and the energy is calculated according to the size of the electrical signal. The WDS is an X-ray detector of a type in which an X-ray is subjected to monochromatic processing (discrimination of energy) by a spectroscope and the monochromatic X-ray is detected by a proportional counter tube and the like.

As the EDS, there are known semiconductor detectors such as an SiLi (silicon lithium) detector, a silicon drift detector, and a germanium detector. For example, the silicon lithium detector and the silicon drift detector are frequently used in an element analyzer of an electron microscope and can detect energy in a wide range of approximately 0.2 keV to 20 keV. However, since silicon is used in the detector, the property thereof depends on a band gap (approximately 1.1 eV) of silicon, in principle. Therefore, it is difficult to improve energy resolution to approximately equal to or greater than 130 eV, and the energy resolution of the EDS is ten or more times inferior to that of the WDS when compared.

When energy resolution which is an index indicating a performance of an X-ray detector is 130 eV, for example, it denotes that energy can be detected with an uncertainty of approximately 130 eV when an X-ray detector is irradiated with an X-ray. Accordingly, as the uncertainty decreases, the energy resolution increases. In other words, when detecting a characteristic X-ray consisting of two spectrums adjacent to each other, if the energy resolution increases, the uncertainty decreases. When an energy difference between two peaks adjacent to each other is approximately 20 eV, the two peaks can be separated at the energy resolution of approximately 20 eV to 30 eV, in principle.

Recently, an energy dispersion-type super-conducting X-ray detector having energy resolution equivalent to that of the WDS is attracting attention. A detector having a super-conducting transition edge sensor (transition edge sensor, hereinafter, referred to as TES) among the super-conducting X-ray detectors is a highly sensitive calorimeter utilizing a rapid resistance change (for example, a temperature change is several mK, and a resistance change is 0.1Ω) of a thin metallic film during a transition between super-conduction and normal conduction. The TES is also called as a micro calorimeter.

The TES detects temperature changes in the TES occurring when a fluorescent X-ray or a characteristic X-ray generated from a sample by being irradiated with radiation such as a primary X-ray and a primary electron ray is incident, thereby analyzing the sample. The TES has higher energy resolution than other detectors. For example, the TES can acquire energy resolution equal to or less than 10 eV in a characteristic X-ray of 5.9 keV, for example.

When the TES is mounted on a scanning electron microscope or a transmission electron microscope, the TES obtains a characteristic X-ray generated from a sample which is irradiated with an electron ray, and thus, it is possible to easily separate peaks of an energy spectrum of a characteristic X-ray (for example, Si-K$\alpha$, W-M$\alpha$, and W-M$\beta$) which cannot be separated by a semiconductor-type X-ray detector.

Since the TES is a highly sensitive calorimeter, multiple sheets of heat shields are necessary to ensure a stable operation. However, since X-rays generated from a sample need to be introduced to the TES, X-ray windows are equipped in the heat shields as described in Non Patent Document 1, which is identified below. In Non Patent Document 1, the X-ray windows are equipped in the heat shields which are individually cooled to 4 K and 80 K. The X-ray window allows an analysis target X-ray to pass through but performs shutting-off against visible light and infrared light which cause noise.

Moreover, apart from the heat shields, in order to make the TES into one vacuum chamber, X-ray windows having vacuum resistant properties are provided so as to perform shielding against the outer atmosphere at room temperature. In general, as the X-ray window having a vacuum resistant property, an X-ray window adopting an organic membrane is utilized as described in Non Patent Document 2, which is identified below. When three sheets of the X-ray windows are equipped, X-ray transmittance thereof greatly drops to equal to or less than 1% (less than 0.2 keV) from 60% (1 keV).

In addition, since the size of an X-ray absorbent provided in the TES is small (several hundred microns), an X-ray lens is provided between a sample and the TES for the purpose of increasing an effective solid angle. A capillary is generally formed with a thin glass tube. This type of configuration is disclosed in: U.S. Pat. No. 5,880,467; JP-B-1995(H07)-040080; JP-B-1995(H07)-011600; and JP-A-2008-039500.

Non Patent Document 1: Keiichi TANAKA et al (nine), "Transition Edge Sensor-Energy Dispersive Spectrometer (TES-EDS) and Its Applications", "IEICE TRANSACTIONS on Electronics", vol. E92-C No. 3, 2009, p. 334 to 340

Non Patent Document 2: AP Ultra-thin Polymer X-ray Windows. [online]. MOXTEK Incorporated, 2010. "retrieved on 2013-10-15". Retrieved from the Internet: <URL: http://moxtek.com/xray-product/ap-windows/>

However, in the X-ray fluorescence analysis apparatus described above, efficiency of X-ray transmittance equal to or less than 1 keV is unfavorable, and for example, detection efficiency of boron (183 eV) is one level lower than the existing silicon drift-type semiconductor detector (silicon drift detector, hereinafter, referred to as SDD). The reason is that the TES requires two or more X-ray windows for heat shields in addition to an X-ray window formed with an organic membrane, compared to one sheet of the X-ray window formed with the organic membrane which is enough for the SDD.

The TES has an operation temperature lower than that of the SDD so that the TES needs to be provided with extra X-ray windows as the heat shields for a stable operation, compared to the SDD. As described above, it is necessary that the TES can be thermally stable and acquire efficiency of X-ray transmittance equivalent to or greater than that of the SDD in order to efficiently obtain an X-ray equal to or less than 1 keV by the TES.

SUMMARY

The present invention has been made in view of the above-described circumstances, and one of objects of the present invention is to provide an X-ray fluorescence analysis apparatus which is shielded from visible light and infrared light, and in which the thickness of an X-ray window can be minimized. As a result, an X-ray equal to or less than 1 keV can be efficiently obtained.

According to an exemplary embodiment of the present invention, there is provided an X-ray fluorescence analysis apparatus is provided with: an excitation source configured to excite an analysis target sample to emit a characteristic X-ray; an X-ray detector configured to detect the characteristic X-ray emitted from the analysis target sample; and an electromagnetic wave shield and a heat shield that are sequentially arranged from the analysis target sample toward the X-ray detector. The electromagnetic wave shield is provided with a through hole portion on which a through hole through which the characteristic X-ray passes is formed, the through hole having a size equal to or smaller than 50 µm. The heat shield is provided with a window portion through which the characteristic X-ray is passed through.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Hereinafter, an X-ray fluorescence analysis apparatus according to an embodiment of the present invention will be described with reference to the accompanied drawings.

For example, an X-ray fluorescence analysis apparatus 10 according to the embodiment can be utilized as a composition analysis apparatus such as an electron microscope, an ion microscope, an X-ray microscope, and an X-ray fluorescence analysis apparatus.

Figure 1:
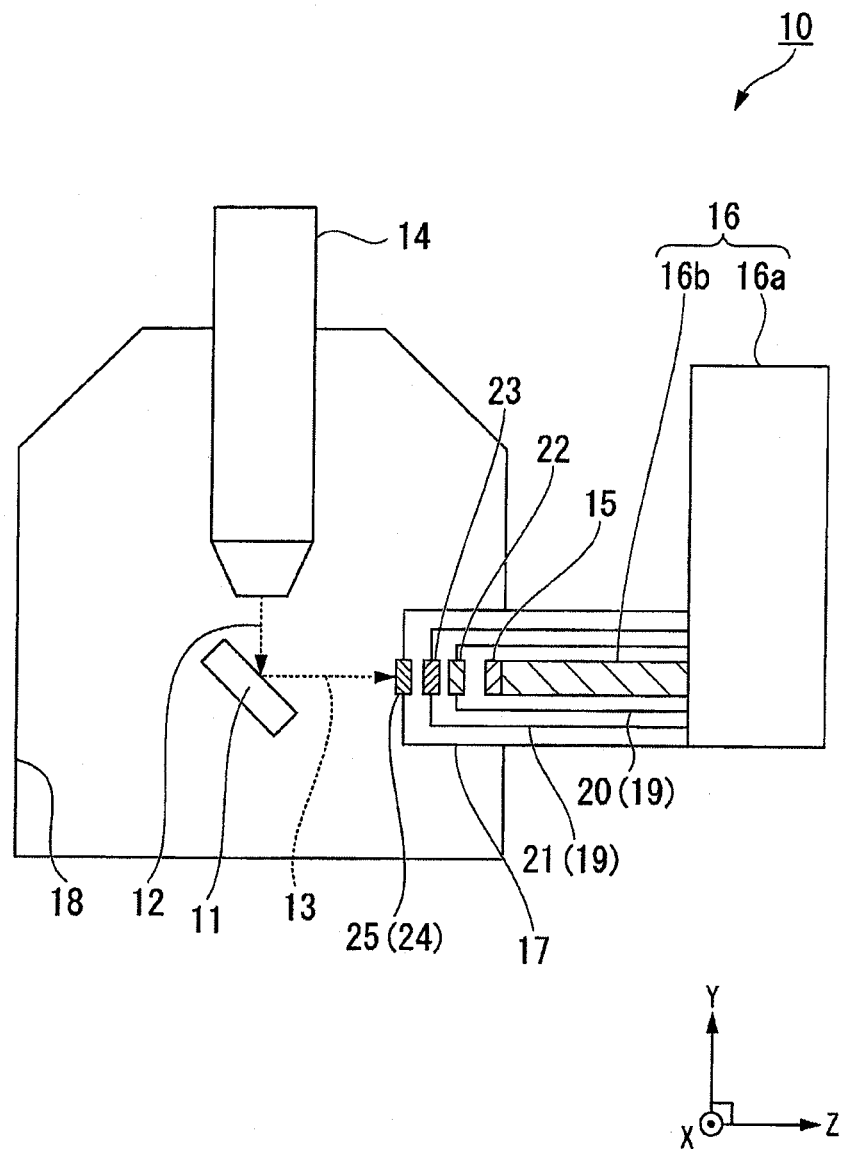
FIG. 1 is a cross-sectional view schematically illustrating a configuration of an X-ray fluorescence analysis apparatus in an embodiment of the present invention.

As illustrated in FIG. 1, the X-ray fluorescence analysis apparatus 10 is provided with an electron gun 14 that causes a sample 11 to be excited by irradiating the analysis target sample 11 with an electron ray 12 and to emit a characteristic X-ray 13 from the sample 11, and a super-conducting transition edge sensor (transition edge sensor, TES) 15 as an X-ray detector that detects the characteristic X-ray 13 emitted from the sample 11.

The TES 15 utilizes super-conducting transition of a super-conductor. The TES 15 holds an operating point in an intermediate state between normal conduction and super-conduction during an operation for detecting an X-ray. Accordingly, when one X-ray is absorbed into the TES 15 in a state where the operating point is held in the midst of a super-conducting transition, resistance changes of several µW can be obtained with respect to temperature fluctuations of 100 mK, for example, thereby making it possible to obtain radiation pulses of µA order. In addition, by storing data regarding a relationship between a pulse peak value and energy of radiation in advance, even though the TES 15 is irradiated with radiation having unknown energy, it is possible to detect the energy of incident radiation through a signal pulse peak value.

The X-ray fluorescence analysis apparatus 10 is provided with a cooling device 16 that cools the TES 15.

The cooling device 16 is provided with a cryocooler 16a and a cold head 16b which is cooled by the cryocooler 16a. The TES 15 is installed at the tip end of the cold head 16b arranged inside a snout 17 which is equipped in the cryocooler 16a and has a heat insulation structure.

The sample 11, the electron gun 14, and a tip end portion of the snout 17 are arranged inside a chamber 18. The inside of the cooling device 16 and the chamber 18 is subjected to vacuum exhaust by using a turbo molecular pump or a diffusion pump. The degree of vacuum ranges from approximately $10^{-3}$ Pa to $10^{-5}$ Pa.

The cryocooler 16a may be configured by a dilution refrigerator or an adiabatic demagnetization refrigerator, for example. A dilution refrigerator performs cooling by utilizing a difference in enthalpy when 3He dissolves from a dense phase to a dilute phase in a mixing chamber. An adiabatic demagnetization refrigerator applies a magnetic field to a magnetic body to align the orientation of spins and cools an object connected to the magnetic body as entropy increases when removing the magnetic field.

The cold head 16b is cooled to a temperature at vicinity of 100 mK by the cryocooler 16a. In order to cool the cold head 16b to 100 mK and to operate the TES 15 in a thermally stable state, the cold head 16b and the TES 15 may be shielded from heat radiation of the snout 17 having room temperature and the like. While being affected by a parameter, the TES 15 generally does not operate when received heat of 100 pW. Therefore, in order to eliminate heat radiation from a high temperature portion to the TES 15, the X-ray fluorescence analysis apparatus 10 is provided with a heat shield 19 having a temperature higher than that of the TES 15.

The heat shield 19 is provided with a first heat shield 20 which is installed so as to cover the TES 15 and the cold head 16b, and a second heat shield 21 which is installed between the first heat shield 20 and the snout 17.

The first heat shield 20 and the second heat shield 21 respectively include a first X-ray window 22 and a second X-ray window 23 which allow the characteristic X-ray 13 emitted from the sample 11 to reach the TES 15.

Each of the first X-ray window 22 and the second X-ray window 23 is formed with a light element material in order to efficiently transmit a low-energy X-ray equal to or less than 1 keV in particular. Each of the first X-ray window 22 and the second X-ray window 23 is thinly formed to a minimum to ensure the desired heat shielding. Each of the first X-ray window 22 and the second X-ray window 23 adopts a laminate type in which aluminum is laminated on an organic membrane or a silicon nitride membrane, for example. Particularly, in order to ensure the desired transmittance with respect to an X-ray equal to or less than 1 keV, the thickness of all of the organic membrane or the silicon nitride membrane and the aluminum is set to be equal to or less than 100 nm. In comparison with the organic membrane, the silicon nitride membrane does not contain oxygen and carbon in the membrane. Therefore, each of oxygen and carbon can be properly analyzed.

Figure 2A:
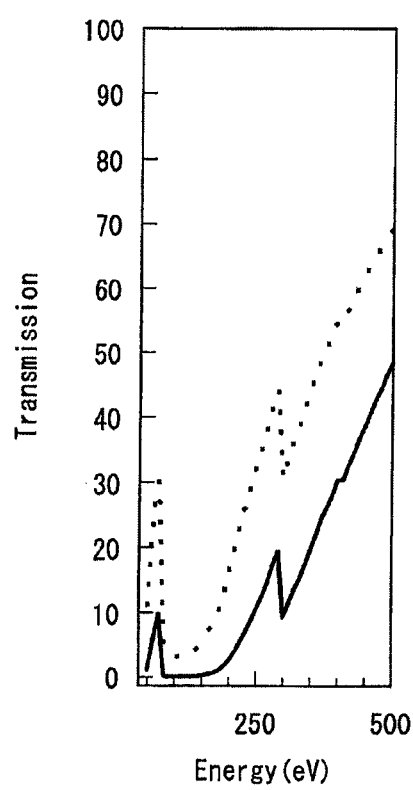
FIGS. 2A and 2B are diagrams illustrating examples of a relationship between energy and a transmittance of an X-ray transmitted through a window portion in the embodiment (FIG. 2A) and a comparative example (FIG. 2B)
Figure 2B:
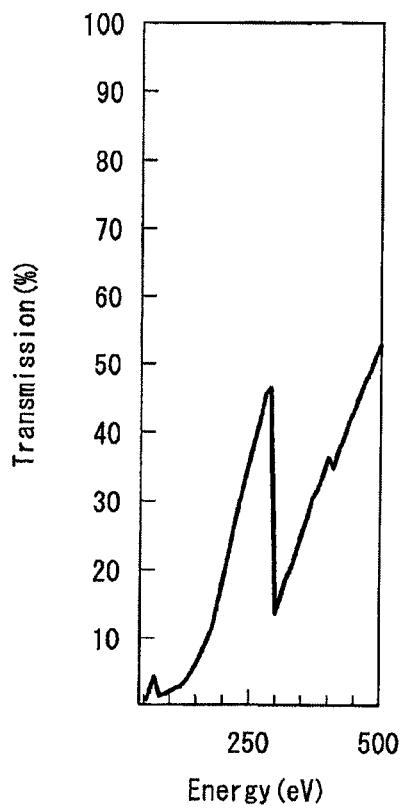

The solid line shown in FIG. 2A indicates a curved line for transmittance corresponding to X-ray energy when each of the first X-ray window 22 and the second X-ray window 23 in the present embodiment is configured as a laminated body of an organic membrane having the thickness of 100 nm and aluminum having the thickness of 100 nm. The dotted line shown in FIG. 2A indicates a curved line for transmittance corresponding to X-ray energy when each of the first X-ray window 22 and the second X-ray window 23 in the present embodiment is configured as a laminated body of an organic membrane having the thickness of 50 nm and aluminum having the thickness of 50 nm. As a comparison example with respect to the present invention, the solid line shown in FIG. 2B indicates an example of a curved line for transmittance of a transmitting membrane by an organic membrane used in a semiconductor-type X-ray detector.

In the case between the solid line in FIG. 2A of the present embodiment and the comparison example, it is confirmed that transmittance of the X-ray in the vicinity of 500 eV is equivalent to each other. In the case between the dotted line in FIG. 2A of the present embodiment and the comparison example, it is confirmed that transmittance of the X-ray in the vicinity of 200 eV is equivalent to each other.

In other words, even though the number of X-ray windows for transmitting a low-energy X-ray equal to or less than 1 keV increases, desired transmittance of an X-ray can be ensured by thinning the thicknesses of aluminum and an organic membrane configuring the X-ray windows.

By adopting the laminate body of aluminum and an organic membrane or a silicon nitride membrane for each of the first X-ray window 22 and the second X-ray window 23, while shutting visible light and infrared light off from being incident on the TES 15, it is possible to obtain an X-ray having energy as low as possible.

In the related art, the effects of shutting visible light and infrared light off decreases if aluminum and the organic membrane are too thinned, causing a problem in that noise of the TES 15 increases due to visible light or infrared light being absorbed into the TES 15. In this case, even though a low-energy X-ray can be obtained, there is a need to shut visible light and infrared light off.

In order to solve the problem, the X-ray fluorescence analysis apparatus 10 of the present embodiment is provided with a capillary 25 as an electromagnetic wave shield 24 that is supported by the snout 17 between the sample 11 and the second X-ray window 23.

The capillary 25 is provided with a through hole portion 27 being formed with a through hole 26 through which the characteristic X-ray 13 emitted from the sample 11 passes. The material of the capillary 25 is nonmetal or metal. For example, the capillary 25 is formed with a thin glass tube.

When the size of the through hole 26 (for example, the diameter or the length of one side) is D (m), and the wavelength of an incident electromagnetic wave is $\lambda$, (m), it is known that an electromagnetic wave having a wavelength longer than $D=\lambda/2$ does not pass through the through hole 26 based on the principle of wavelength limit. For example, when energy E of an electromagnetic wave is 0.01 eV, D=62 μm. In other words, in a case of D=62 μm, shielding is performed by the capillary 25 against an electromagnetic wave having energy equal to or less than 0.01 eV. In a case of D=6.2 μm, shielding is performed by the capillary 25 against an electromagnetic wave having energy equal to or less than 0.1 eV.

The capillary 25 serves to concentrate the characteristic X-ray 13.

In the X-ray fluorescence analysis apparatus 10 of the present embodiment, the size of the through hole 26 may be formed to be at least equal to or less than 50 μm. Particularly, when energy of the characteristic X-ray 13 to be obtained is equal to or greater than 1 eV, the size may be formed to be D=10 μm.

Since the capillary 25 does not perform shielding against an X-ray contrary to each of the first X-ray window 22 and the second X-ray window 23 formed with the laminated body of aluminum and an organic membrane or a silicon nitride membrane, the capillary 25 effectively obtains the analysis target characteristic X-ray 13 equal to or less than 1 keV while suppressing attenuation of the characteristic X-ray 13. By adopting the capillary 25 as the shielding against visible light and infrared light, there may be no need to provide a function for shutting visible light and infrared light off for an X-ray window as in the related art. Accordingly, the number and thickness of the X-ray windows adopted for shutting visible light and infrared light off can be reduced.

Each of the first X-ray window 22 and the second X-ray window 23 not only transmits the characteristic X-ray 13 emitted from the sample 11 but also functions as a heat shield to operate the TES 15 in a thermally stable state.

Figure 3:
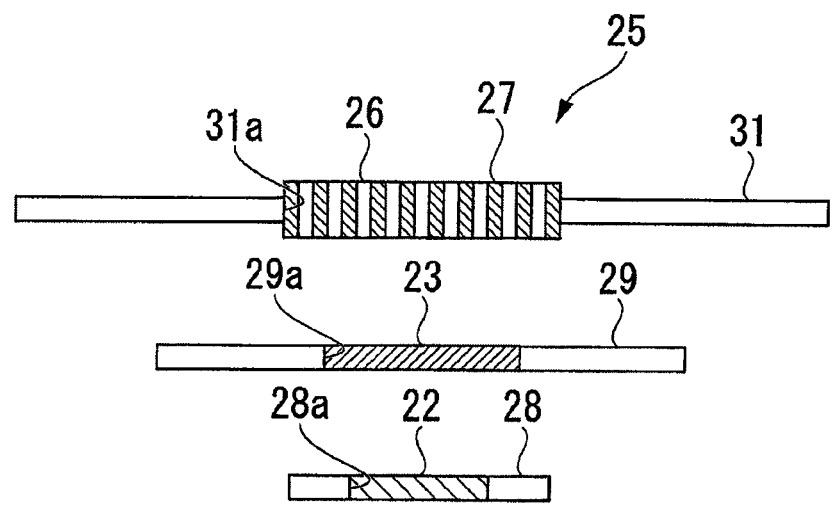
FIG. 3 is a cross-sectional view schematically illustrating configurations of first and second metal plates and first and second X-ray windows in the embodiment.

Each of the first X-ray window 22 and the second X-ray window 23 is supported by a metal plate having high heat conductivity, for example. As illustrated in FIG. 3, the first X-ray window 22 is equipped in a through hole 28a provided at a portion of a first metal plate 28 installed at the tip end portion of the first heat shield 20. The second X-ray window 23 is equipped in a through hole 29a provided at a portion of a second metal plate 29 installed at the tip end portion of the second heat shield 21. The first metal plate 28 and the second metal plate 29 may be integrally formed with the first heat shield 20 and the second heat shield 21 respectively.

Since the heat conductivity of the first metal plate 28 and the second metal plate 29 is formed to be respectively higher than the heat conductivity of the first X-ray window 22 and the second X-ray window 23, it is preferable that each of the first X-ray window 22 and the second X-ray window 23 be formed to have a minimum size in a state where an effective desired solid angle between the sample 11 and the TES 15 is ensured.

For example, the capillary 25, the second X-ray window 23, and the first X-ray window 22 which are sequentially arranged from the sample 11 toward the TES 15 may be formed to be arranged on the same straight line so as to gradually decrease in size in order, or may be formed to have the same size.

For example, when the capillary 25, the second X-ray window 23, and the first X-ray window 22 are formed to gradually decrease in size, the size of each of the second X-ray window 23 and the first X-ray window 22 is formed to be smaller than the size of a through hole 31a to which the capillary 25 is equipped in a metal plate 31 by equal to or greater than 1 mm since the temperature of each of the second X-ray window 23 and the first X-ray window 22 becomes lower than the temperature (for example, room temperature) of the metal plate 31 supporting the capillary 25.

The TES 15 is cooled to a temperature of approximately 100 mK by the cooling device 16 and generates heat of several tens of pW due to a constant current flowing in the TES 15 at all times.

Figure 4:
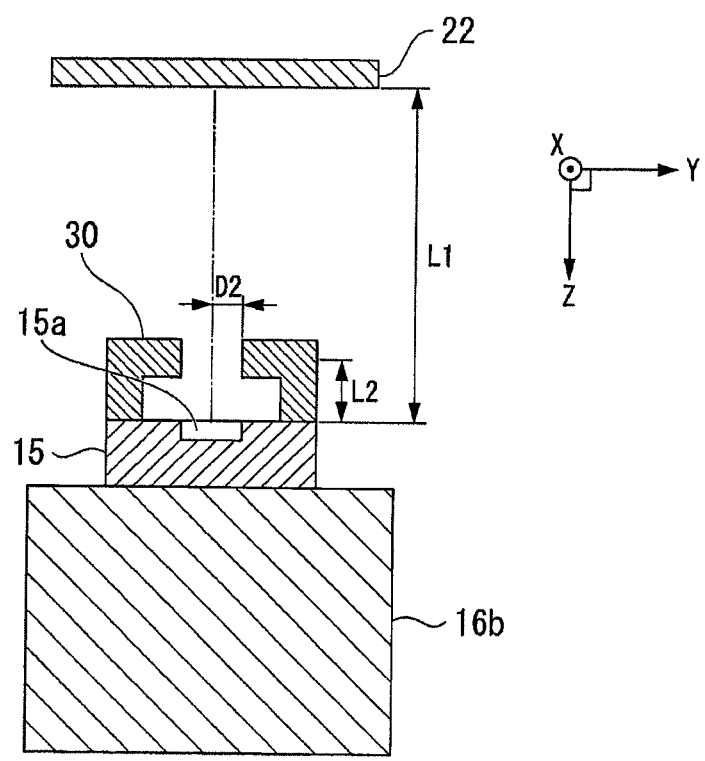
FIG. 4 is a cross-sectional view schematically illustrating a configuration of a tip end portion of a cold head in the embodiment.

As illustrated in FIG. 4, the X-ray fluorescence analysis apparatus 10 of the present embodiment may be provided with a collimator 30 having an opening radius D2 at a position in front of the TES 15 in a direction from the sample 11 toward the TES 15 (for example, Z-direction). In this case, the X-ray fluorescence analysis apparatus 10 has a distance L2 between the TES 15 and the collimator 30, and a distance L1 between the TES 15 and the first X-ray window 22.

In addition, from a viewpoint of radiant heat, when the TES 15 and the first metal plate 28 face each other, it is desirable that the portions facing each other be metal. For example, when an absorbent 15a in the TES 15 absorbing an X-ray is formed with gold, and the first metal plate 28 supporting the first X-ray window 22 is formed with aluminum, it is known that emissivity of both metals ($\epsilon$1 and $\epsilon$2) is approximately 0.02 to 0.03 (see, for example, written by Hiroyasu. Hagiwara, "Outline of Cryogenic Engineering", Publishing Office in Tokyo Denki University, 1999, refer to page 264).

In this case, an area S1 through which the TES 15 views the first X-ray window 22 is expressed as in the following Expression (1), for example.

$$S1 = \pi (L2/L1) \times D2)^2 \quad (1)$$

For example, S1=12.56×10 mm², according to the above Expression (1), when L2=200 μm, D2=100 μm, and L1=2,000 μm.

For example, a heat radiation Q from the first X-ray window 22 to the TES 15 is expressed as in the following Expression (2) based on the Stefan-Bolzmann constant σ, an area S2 of the TES 15, and temperatures $T_1$ and $T_2$ of the TES 15 and the first X-ray window 22.

$$Q = \sigma(T_1^4 - T_2^4)S1 \times \frac{1}{\frac{1}{\varepsilon_1} + \frac{S2}{S1}\left(\frac{1}{\varepsilon_2} - 1\right)} \quad (2)$$

Figure 5A:
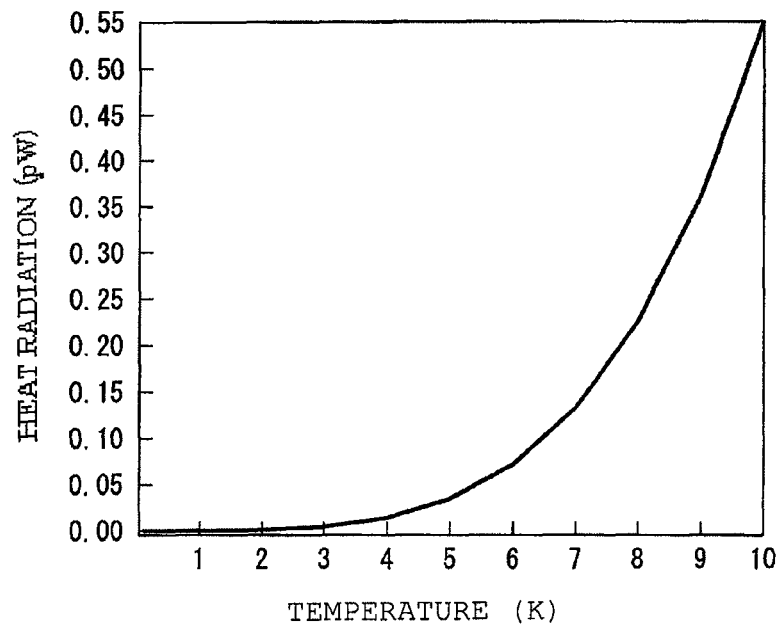
FIGS. 5A and 5B are diagrams illustrating a calculation result (FIG. 5A) of heat radiation from the first X-ray window to a TES and a calculation result (FIG. 5B) of heat radiation from the second X-ray window and the second metal plate to the first X-ray window and the first metal plate in the embodiment.

A calculation result of heat radiation from the first X-ray window 22 to the TES 15 is illustrated in FIG. 5A. When the first X-ray window 22 is equal to or less than 10 K, the radiant heat is approximately equal to or less than 1 pW, which is equal to or less than 1/10 of the calorific value of the TES 15. In other words, radiant heat from the first X-ray window 22 to the TES 15 can be ignored. Thus, the TES 15 can be stably operated. A still shield (<1 K) inside a dilution refrigerator may be used as a method of cooling the first X-ray window 22 to equal to or less than 10 K.

The X-ray fluorescence analysis apparatus 10 of the present embodiment is set to 1 K in a state where the first metal plate 28 and the first X-ray window 22 are cooled to a maximum temperature. The first X-ray window 22 on the TES 15 side is formed with a metal membrane such as aluminum. However, in order to reflect heat radiation from the second metal plate 29 as much as possible, it is preferable that the first X-ray window 22 on the second metal plate 29 side be also provided with a metal membrane such as aluminum.

The cooling ability of a still shield inside a dilution refrigerator depends on a performance of the refrigerator. However, the cooling ability is equal to or greater than several hundreds of μW in general. Therefore, heat radiation from the second X-ray window 23, the second metal plate 29, and the second heat shield 21 to the first X-ray window 22, the first metal plate 28, and the first heat shield 20 may be set to be equal to or less than several hundreds of μW.

Figure 5B:
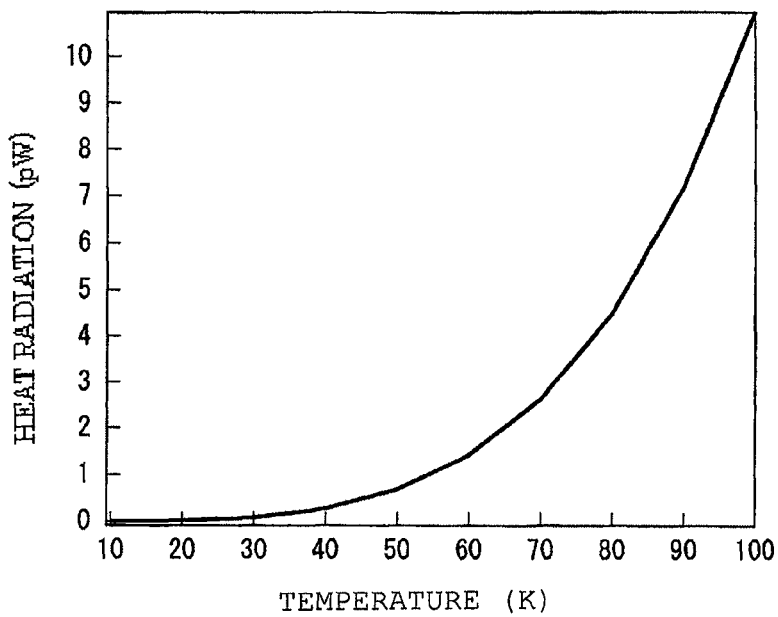

FIG. 5B illustrates a calculation result of heat radiation from the second X-ray window 23 and the second metal plate 29 to the first X-ray window 22 and the first metal plate 28 when the temperatures of the second X-ray window 23 and the second metal plate 29 are set to range from 10 K to 100 K.

In the X-ray fluorescence analysis apparatus 10 of the present embodiment, the first metal plate 28 and the second metal plate 29 are circularly shaped. The diameter of the first metal plate 28 is 10 mm, and the diameter of the second metal plate 29 is 20 mm. However, there is no need to make the first metal plate 28 and the second metal plate 29 be circularly shaped. As described above, when the temperature of the second metal plate 29 does not exceed 100 K, the maximum heat radiation from the second X-ray window 23 and the second metal plate 29 to the first X-ray window 22 and the first metal plate 28 is approximately 10 μW.

Subsequently, heat radiation from the second heat shield 21 to the first heat shield 20 will be described.

In the X-ray fluorescence analysis apparatus 10 of the present embodiment, N-layers of thermal insulation (not illustrated) to shut radiant heat off may be provided between the first heat shield 20 and the second heat shield 21. Accordingly, a heat input from a high temperature portion to a low temperature portion can be reduced to 1/(N+1). For example, when the length of the first heat shield 20 in the Z-direction is 200 mm, the length of the second heat shield 21 in the Z-direction is 250 mm, the temperature of the second heat shield 21 is 100 K, and N=10, an amount of heat input from the second heat shield 21 to the first heat shield 20 is equal to or less than 0.6 μW. As described above, heat radiation from the second heat shield 21, the second metal plate 29, and the second X-ray window 23 to the first heat shield 20, the first metal plate 28, and the first X-ray window 22 is approximately less than 100 μW, which is sufficiently lower than the cooling ability of the still shield.

Subsequently, heat radiation from the snout 17 to the second metal plate 29, the second X-ray window 23, and the second heat shield 21 will be described.

In the X-ray fluorescence analysis apparatus 10 of the present embodiment, the temperature is 10 K when the second metal plate 29, the second X-ray window 23, and the second heat shield 21 are cooled to the maximum temperatures. As illustrated in FIG. 3, the capillary 25 and the metal plate 31 for supporting the capillary 25 are provided at the tip end of the snout 17.

Firstly, heat radiation from the capillary 25 and the metal plate 31 to the second metal plate 29 and the second X-ray window 23 will be described.

In the X-ray fluorescence analysis apparatus 10 of the present embodiment, the through hole 31a is provided at the center portion of the metal plate 31, and the capillary 25 is equipped on a inner wall of the through hole 31a. For example, when the diameter of the metal plate 31 is 30 mm, and the diameter of the capillary 25 is 10 mm, heat radiation from the capillary 25 and the metal plate 31 to the second metal plate 29 and the second X-ray window 23 is approximately 4 mW.

Subsequently, heat radiation from the snout 17 to the second heat shield 21 will be described.

For example, when the length of the second heat shield 21 is 250 mm, the length of the snout 17 is 300 mm, the temperature of the snout 17 is 300 K, and N=10, an amount of heat input from the snout 17 to the second heat shield 21 is approximately 120 µW. Therefore, heat radiation from the snout 17, the metal plate 31, and the capillary 25 to the second metal plate 29, the second X-ray window 23, and the second heat shield 21 is equal to or less than 10 mW.

In the X-ray fluorescence analysis apparatus 10 of the present embodiment, a first shield and the like of a mechanical refrigerator which is used for precooling a dilution refrigerator may be adopted as a method of cooling the second metal plate 29, the second X-ray window 23, and the second heat shield 21. As an example of a mechanical refrigerator, there is a GM refrigerator. A first shield of the GM refrigerator can perform cooling to approximately 40 K, and the cooling ability thereof is several Ws. Therefore, the first shield of the GM refrigerator can sufficiently cool the second metal plate 29, the second X-ray window 23, and the second heat shield 21.

As described above, according to the X-ray fluorescence analysis apparatus 10 of the present embodiment, the capillary 25 as the electromagnetic wave shield 24, and the first X-ray window 22 and the second X-ray window 23 as the heat shields 19 are sequentially arranged in a direction from the sample 11 to the TES 15 (for example, Z-direction). In other words, the capillary 25 allows the characteristic X-ray 13 to pass through and performs shielding against electromagnetic waves other than the characteristic X-ray 13 such as visible light and infrared light. The first X-ray window 22 and the second X-ray window 23 allows the characteristic X-ray 13 to be transmitted and shields the TES 15 from heat radiation.

Accordingly, there may be no need to provide a function to be shielded from electromagnetic waves other than the characteristic X-ray 13 for the first X-ray window 22 and the second X-ray window 23 transmitting the characteristic X-ray 13. Therefore, the thicknesses of each of the first X-ray window 22 and the second X-ray window 23 and the number of X-ray windows necessary can be decreased to a minimum required for the heat shielding. Thus, it is possible to suppress attenuation of transmittance of the characteristic X-ray 13.

Moreover, while attenuation of the characteristic X-ray 13 is suppressed or prevented, the capillary 25 allows the characteristic X-ray 13 to pass through and can perform shielding against electromagnetic waves other than the characteristic X-ray 13 such as visible light and infrared light.

In addition, when the capillary 25, the second X-ray window 23, and the first X-ray window 22 are formed to gradually decrease in size in this order, it is possible to improve collimation of characteristic X-rays and shielding against infrared rays and visible rays of light other than characteristic X-rays.

Accordingly, even at a low energy region of approximately 10 eV in an energy region equal to or less than 1 keV, shielding is performed against infrared rays and visible rays of light affecting as noise, and the TES 15 is operated in a thermally stable state. Thus, it is possible to efficiently obtain the characteristic X-ray 13 of low energy.

First Modification Example

Figure 6:
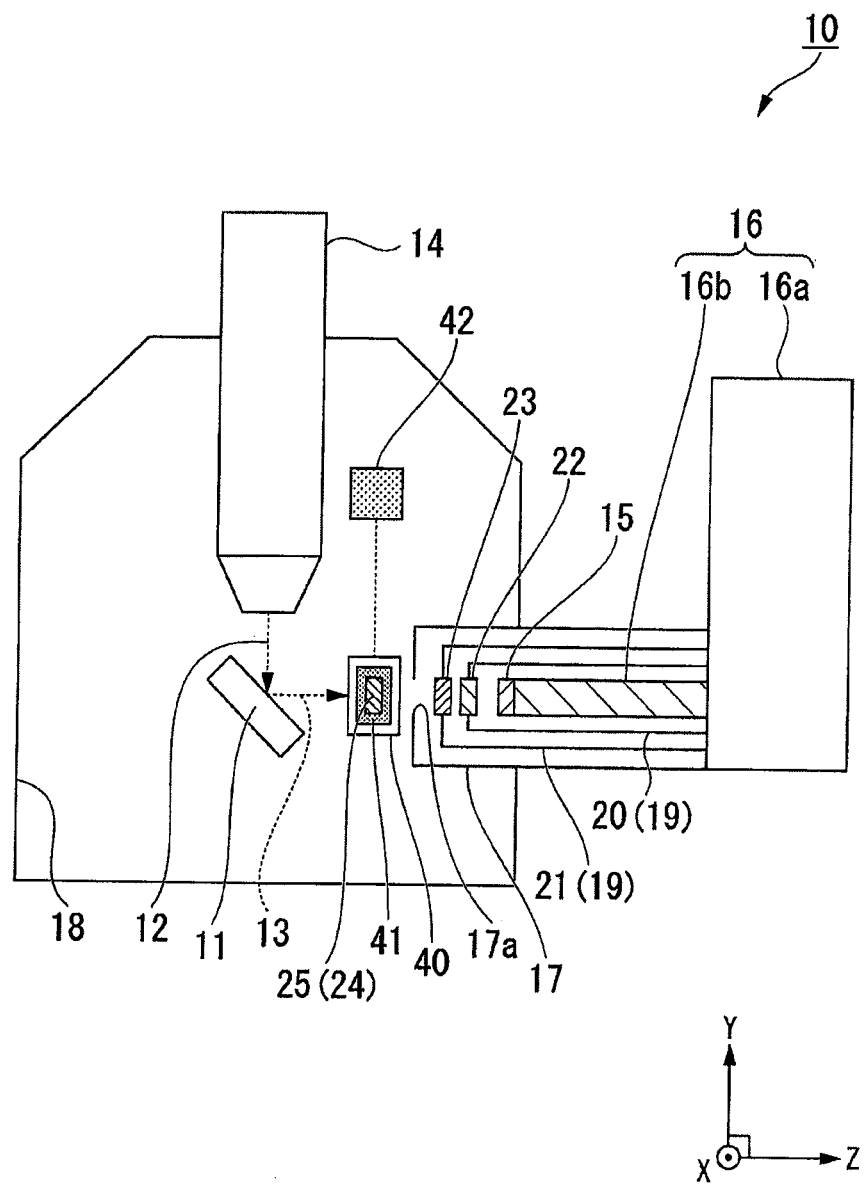
FIG. 6 is a cross-sectional view schematically illustrating a configuration of the X-ray fluorescence analysis apparatus in a first modification example of the embodiment.

In the embodiment described above, as illustrated in FIG. 6, the capillary 25 may be supported by a separated capillary adjustment mechanism 40 without being fixed to the metal plate 31. In this case, an opening 17a through which the characteristic X-ray 13 passes is provided at the tip end portion of the snout 17.

A capillary adjustment mechanism 40 can adjust a position of the capillary 25 within a plane (for example, within an XY-plane) which is orthogonal to a direction (for example, Z-direction) from the sample 11 toward the TES 15. In addition, without being limited to the range of the XY-plane, the capillary adjustment mechanism 40 may also be able to adjust a position of the capillary 25 in the Z-direction.

An insulator 41 for decreasing heat conductivity between the capillary 25 and the capillary adjustment mechanism 40 may be provided as necessary, thereby cooling the capillary 25 by a separated cooling mechanism 42.

For example, as described above, when heat radiation from the capillary 25 and the metal plate 31 to the second metal plate 29 and the second X-ray window 23 is approximately 4 mW, 98% thereof is radiant heat from the capillary 25. Therefore, the capillary 25 is cooled to be at least equal to or less than 200 K. For example, since the capillary 25 is cooled to 77 K when being cooled by using liquid nitrogen, heat radiation from the capillary 25 to the second metal plate 29 and the second. X-ray window 23 can be decreased to ½₀₀. As a result, cooling of the capillary 25 is effective to operate the TES 15 in a thermally stable state.

The cooling mechanism 42 may be accommodated in the chamber 18. Otherwise, a main body may be arranged outside the chamber 18 while only a portion of the section for cooling the capillary 25 is accommodated inside the chamber 18.

Second Modification Example

Figure 7:
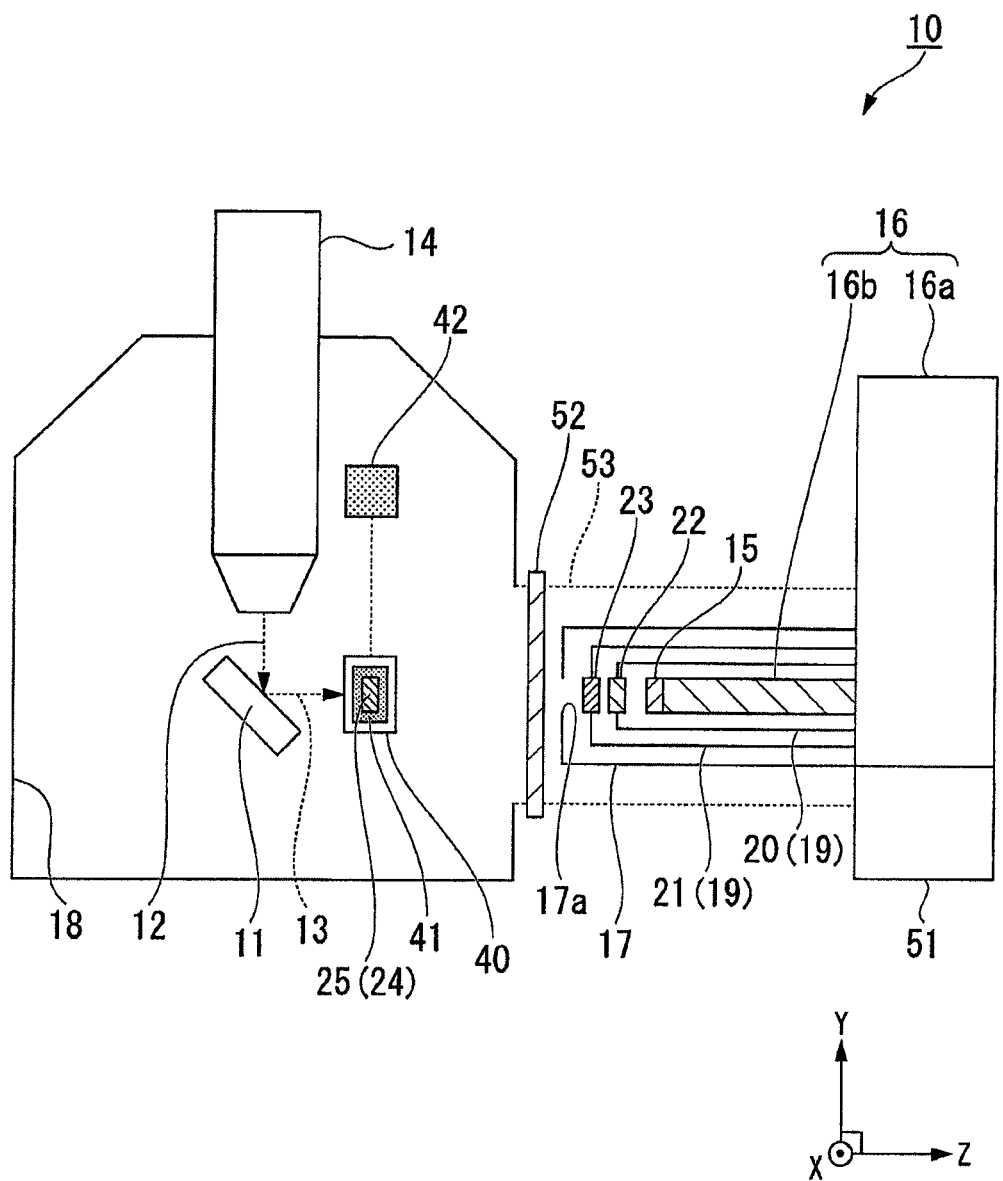
FIG. 7 is a cross-sectional view schematically illustrating a configuration of the X-ray fluorescence analysis apparatus in a second modification example of the embodiment.

In the embodiment described above, as illustrated in FIG. 7, the capillary 25 may be supported by the capillary adjustment mechanism 40. A cooling position adjustment mechanism 51 which adjusts a position of the cooling device 16 may be included as well as the first metal plate 28, the second metal plate 29, and the TES 15.

Moreover, a shut-off valve 52 which separates a vacuum space between the capillary adjustment mechanism 40 and the cooling position adjustment mechanism 51 may be included. A bellows 53 which maintains a vacuum state of the cooling device 16 and the chamber 18 may be included.

For example, when the cooling device 16 is vacuumed in a state where the chamber 18 of an electron microscope including the electron gun 14, and the cooling device 16 are released to the atmosphere, since the first X-ray window 22 and the second X-ray window 23 are provided to be thin, rapid vacuuming may cause damage to each of the first X-ray window 22 and the second X-ray window 23.

Since the exhaust speed of a vacuum pump utilized in an electron microscope depends on the performance of the pump, it is difficult to adjust the exhaust speed thereof. However, it is desirable that the cooling device 16 including each of the first X-ray window 22 and the second X-ray window 23 provided to be thin be exhausted slowly so as not to generate a differential pressure in the front and back of each of the first X-ray window 22 and the second X-ray window 23. Therefore, it may be important to provide the shut-off valve 52 between the chamber 18 and the cooling device 16 of the electron microscope and to vacuum the chamber 18 and the cooling device 16 independently.

In addition, vacuuming can be slowly performed by providing a needle (not illustrated) which regulates a flow rate when vacuuming the cooling device 16 side.

After vacuuming of the chamber 18 and the cooling device 16 is completed, the shut-off valve 52 is opened, and the cooling device 16 is moved to a predetermined position where the characteristic X-ray 13 emitted from the sample 11 can be obtained. As a result, vacuum states of the chamber 18 and the cooling device 16 can be shut off. Thus, there is no need to release the cooling device 16 to the atmosphere, and only the chamber 18 can be independently released to the atmosphere.

The technical scope of the present invention is not limited to the embodiments described above and includes various changes added to the embodiments described above without departing from the scope and spirit of the invention. In other words, the configurations of the embodiments described above are merely examples. Therefore, various modifications and changes can be made.

For example, in the embodiments described above, the electromagnetic wave shield 24 includes the capillary 25. However, without being limited thereto, a plate-shaped or reticular member having a through hole through which the characteristic X-ray 13 passes may be included.

For example, in the embodiments described above, two X-ray windows such as the first X-ray window 22 and the second X-ray window 23 are included. However, without being limited thereto, more than two (for example, three) X-ray windows may be included.

For example, in the embodiments described above, the collimator 30 is included in the TES 15. However, without being limited thereto, the collimator 30 may be fixed to the cold head 16b.

As described in the above with reference to the embodiment and modification examples, there are provided at least the following aspects.

(1) An X-ray fluorescence analysis apparatus that is provided with: an excitation source configured to excite an analysis target sample to emit a characteristic X-ray; an X-ray detector configured to detect the characteristic X-ray emitted from the analysis target sample; and an electromagnetic wave shield and a heat shield that are sequentially arranged from the analysis target sample toward the X-ray detector. The electromagnetic wave shield is provided with a through hole portion on which a through hole through which the characteristic X-ray passes is formed, the through hole having a size equal to or smaller than 50 µm. The heat shield is provided with a window portion through which the characteristic X-ray is passed through.

(2) In the X-ray fluorescence analysis apparatus according to (1), the window portion of the heat shield may be configured to have a size equal to or smaller than a size of the through hole portion.

(3) In the X-ray fluorescence analysis apparatus according to (2), the heat shield may be configured to have one or more of the window portion, and a size of each window portion may be configured to be smaller as a distance from the through hole portion becomes larger and to be smaller than a size of the through hole portion.

(4) In the X-ray fluorescence analysis apparatus according to any one of (1) to (3), the through hole may be configured to have a size equal to or smaller than 10 µm.

(5) In the X-ray fluorescence analysis apparatus according to any one of (1) to (4), the heat shield may be configured to have three or less window portions which are sequentially arranged from the electromagnetic wave shield toward the X-ray detector.

(6) In the X-ray fluorescence analysis apparatus according to (5), the heat shield may be configured to have two or less window portions which are sequentially arranged from the electromagnetic wave shield toward the X-ray detector.

(7) In the X-ray fluorescence analysis apparatus according to (5) or (6), the electromagnetic wave shield may be provided with a hole portion to which the through hole portion is equipped, and the window portion may be configured to have a size smaller than a size of the hole portion by 1 mm or more.

(8) The X-ray fluorescence analysis apparatus according to (5) or (6) may further be provided with a cooling device configured to cool a first window portion to a temperature equal to or lower than 10K, the first window portion being the window portion closest to the X-ray detector among a plurality of the window portions is equal to or less than 10 K, and to cool a second a second window portion to a temperature equal to or lower than 100K, the second window portion being the window portion adjacent to the first window portion.

(9) In the X-ray fluorescence analysis apparatus according to any one of (1) to (8), the window portion may be configured by a laminated body of metal and an organic membrane or a silicon nitride membrane, and the thickness of each of the metal and the organic membrane or the silicon nitride membrane is configured to be equal to or less than 100 nm.

(10) In the X-ray fluorescence analysis apparatus according to any one of (1) to (9), the electromagnetic wave shield may be configured to concentrate the characteristic X-ray.

(11) The X-ray fluorescence analysis apparatus according to any one of (1) to (10) may further be provided with a shield cooling device configured to cool the electromagnetic wave shield to a temperature equal to or less than 200 K.

(12) The X-ray fluorescence analysis apparatus according to any one of (1) to (11) may further be provided with a shield position adjustment mechanism configured to adjust a position of the electromagnetic wave shield between the analysis target sample and the X-ray detector; a cooling position adjustment mechanism configured to adjust a cooling position at which the cooling device cools the window portion and the X-ray detector; and a shut-off valve configured to separate a vacuum space between the shield position adjustment mechanism and the cooling position adjustment mechanism.

In an X-ray fluorescence analysis apparatus according to an aspect in (1) described above, an electromagnetic wave shield having a through hole through which a characteristic X-ray passes can perform shielding against infrared rays and visible rays of light other than characteristic X-rays. Accordingly, there is no need to provide a function to be shielded from infrared rays and visible rays of light other than characteristic X-rays for window portions of heat shields transmitting the characteristic X-ray. Therefore, the thicknesses of the window portions and the number of window portions can be decreased to a minimum required for the heat shielding. Thus, it is possible to suppress attenuation of the characteristic X-ray when transmitting through the window portions. Accordingly, it is possible to efficiently obtain a characteristic X-ray equal to or less than 1 keV.

Moreover, in the case of (2) or (3) described above, it is possible to improve collimation of characteristic X-rays and shielding against infrared rays and visible rays of light other than characteristic X-rays.

Moreover, in the case of (4) described above, the size (for example, the diameter or the length of one side) of the through hole through which the characteristic X-ray passes is set to equal to or less than 10 µm, and thus, even at a low energy region of approximately 10 eV in an energy region equal to or less than 1 keV, it is possible to perform shielding against infrared rays and visible rays of light affecting as noise.

Moreover, in the case of (5) or (6) described above, three or less window portions, or two or less window sections transmitting the characteristic X-ray are provided, and thus, it is possible to improve efficiency in obtaining a low energy characteristic X-ray.

Moreover, in the case of (7) described above, it is possible to suppress damage to the window portions due to a temperature decrease.

Moreover, in the case of (8) described above, the temperature is lowered in stages through multiple window portions from the surrounding atmosphere of an analysis target sample toward the X-ray detector, and thus, it is possible to prevent a temperature increase of the X-ray detector due to heat radiation and to ensure desired operation characteristics.

Moreover, in the case of (9) described above, while suppressing the efficiency in obtaining the characteristic X-ray equal to or less than 1 keV from decreasing, it is possible to perform effective heat shielding with respect to the X-ray detector. In addition, since a silicon nitride membrane does not contain oxygen and carbon in the membrane, it is possible to properly analyze each of oxygen and carbon.

Moreover, in the case of (10) described above, it is possible to improve efficiency of concentrating the characteristic X-ray.

Moreover, in the case of (11) described above, heat radiation from the electromagnetic wave shield to the window portion can be reduced, and thus, it is possible to further decrease the thicknesses of window portions necessary for the desired heat shielding, and the number of window portions. In addition, it is possible to improve operational stability of the X-ray detector.

Moreover, in the case of (12) described above, the vacuum state of the X-ray detector can be controlled independently from other devices, and thus, it is possible to improve operational stability of the X-ray detector.

What is claimed is:
1. An X-ray fluorescence analysis apparatus comprising:
an excitation source configured to excite an analysis target sample to emit a characteristic X-ray;
an X-ray detector configured to detect the characteristic X-ray emitted from the analysis target sample; and
an electromagnetic wave shield and a heat shield that are sequentially arranged from the analysis target sample toward the X-ray detector,
wherein the electromagnetic wave shield comprises a through hole portion on which a through hole through which the characteristic X-ray passes is formed, the through hole having a size equal to or smaller than 50 µm, and
wherein the heat shield comprises a window portion through which the characteristic X-ray is passed through.

2. The X-ray fluorescence analysis apparatus according to claim 1,
wherein the window portion of the heat shield is configured to have a size equal to or smaller than a size of the through hole portion.

3. The X-ray fluorescence analysis apparatus according to claim 2,
wherein the heat shield is configured to have one or more of the window portion, and
wherein a size of each window portion is configured to be smaller as a distance from the through hole portion becomes larger and to be smaller than a size of the through hole portion.

4. The X-ray fluorescence analysis apparatus according to claim 1,
wherein the through hole is configured to have a size equal to or smaller than 10 µm.

5. The X-ray fluorescence analysis apparatus according to claim 1,
wherein the heat shield is configured to have three or less window portions which are sequentially arranged from the electromagnetic wave shield toward the X-ray detector.

6. The X-ray fluorescence analysis apparatus according to claim 5,
wherein the heat shield is configured to have two or less window portions which are sequentially arranged from the electromagnetic wave shield toward the X-ray detector.

7. The X-ray fluorescence analysis apparatus according to claim 5,
wherein the electromagnetic wave shield is provided with a hole portion to which the through hole portion is equipped, and
wherein the window portion is configured to have a size smaller than a size of the hole portion by 1 mm or more.

8. The X-ray fluorescence analysis apparatus according to claim 5 further comprising:
a cooling device configured to cool a first window portion to a temperature equal to or lower than 10K, the first window portion being the window portion closest to the X-ray detector among a plurality of the window portions is equal to or less than 10 K, and to cool a second a second window portion to a temperature equal to or lower than 100K, the second window portion being the window portion adjacent to the first window portion.

9. The X-ray fluorescence analysis apparatus according to claim 1,
wherein the window portion is configured by a laminated body of metal and an organic membrane or a silicon nitride membrane, and the thickness of each of the metal and the organic membrane or the silicon nitride membrane is configured to be equal to or less than 100 nm.

10. The X-ray fluorescence analysis apparatus according to claim 1, wherein the electromagnetic wave shield is configured to concentrate the characteristic X-ray.

11. The X-ray fluorescence analysis apparatus according to claim 1 further comprising:
a shield cooling device configured to cool the electromagnetic wave shield to a temperature equal to or less than 200 K.

12. The X-ray fluorescence analysis apparatus according to claim 1 further comprising:
a shield position adjustment mechanism configured to adjust a position of the electromagnetic wave shield between the analysis target sample and the X-ray detector;
a cooling position adjustment mechanism configured to adjust a cooling position at which the cooling device cools the window portion and the X-ray detector; and
a shut-off valve configured to separate a vacuum space between the shield position adjustment mechanism and the cooling position adjustment mechanism.

* * * * *